(12) United States Patent
Heaton (10) Patent No.: US 6,960,913 B2
(45) Date of Patent: Nov. 1, 2005

(54) MULTI-MEASUREMENT NMR ANALYSIS BASED ON MAXIMUM ENTROPY

(75) Inventor: Nicholas J. Heaton, Houston, TX (US)

(73) Assignee: Schlumberger Technology Corporation, Sugar Land, TX (US)

(*) Notice: Subject to any disclaimer, the term of this patent is extended or adjusted under 35 U.S.C. 154(b) by 95 days.

(21) Appl. No.: 10/675,556

(22) Filed: Sep. 30, 2003

(65) Prior Publication Data

US 2005/0040822 A1 Feb. 24, 2005

Related U.S. Application Data

(60) Provisional application No. 60/439,873, filed on Jan. 14, 2003.

(51) Int. Cl.⁷ .................................................. G01V 3/00
(52) U.S. Cl. ..................................................... 324/303
(58) Field of Search ........................ 324/303, 333–343, 324/345–346, 351–352, 355–356, 366–369, 300, 308–310, 313, 315, 307

(56) References Cited

U.S. PATENT DOCUMENTS

| | | | |
|---|---|---|---|
| 5,363,041 A | 11/1994 | Sezginer | |
| 6,121,774 A | 9/2000 | Sun et al. | |
| 6,166,543 A | 12/2000 | Sezginer et al. | |
| 6,229,308 B1 | 5/2001 | Freedman | |
| 6,232,778 B1 | 5/2001 | Speier et al. | |
| 6,255,818 B1 | 7/2001 | Heaton et al. | |
| 6,400,147 B1 | 6/2002 | Toufaily et al. | |
| 6,459,992 B1 | 10/2002 | Freedman et al. | |
| 6,498,484 B1 | 12/2002 | Sun et al. | |
| 6,518,757 B1 | 2/2003 | Speier | |
| 6,522,137 B1 | 2/2003 | Sun et al. | |
| 6,522,138 B2 | 2/2003 | Heaton | |
| 6,534,980 B2 | 3/2003 | Toufaily et al. | |
| 6,559,638 B1 | 5/2003 | Adelerhof | |
| 6,573,716 B2 | 6/2003 | Toufaily et al. | |
| 2002/0067164 A1 | 6/2002 | Venkataramanan et al. | |
| 2002/0105326 A1 * | 8/2002 | Hurlimann et al. | 324/303 |

FOREIGN PATENT DOCUMENTS

| | | |
|---|---|---|
| GB | 2394058 | 4/2004 |
| GB | 2395013 | 5/2004 |
| GB | 2398876 | 9/2004 |
| WO | WO02/095450 | 11/2002 |

OTHER PUBLICATIONS

Hurlimann, M.D. et al., Quantitative Measurement of Two–Dimensional Distribution Functions of Diffusion and Relaxation in Grossly Inhomogenous Fields, Journal of Magnetic Resonance, vol. 157, Jul. 2002, pp. 31–42.

* cited by examiner

*Primary Examiner*—Bot LeDynh
(74) *Attorney, Agent, or Firm*—Kevin P. McEnaney; Victor H. Sagura; Brigitte L. Echols (57) ABSTRACT

A method is disclosed for extracting information about a system of nuclear spins from a region of an earth formation. Specifically, a set of NMR data is acquired for a fluid sample located either in a borehole or in a laboratory environment. From the set of NMR data, a multi-dimensional distribution is calculated using a mathematical inversion that is independent of prior knowledge of fluid sample properties.

28 Claims, 6 Drawing Sheets

MULTI-MEASUREMENT NMR ANALYSIS BASED ON MAXIMUM ENTROPY

CROSS REFERENCE TO RELATED APPLICATIONS

This invention claims priority pursuant to 35 U.S.C. §119 of U.S. Provisional Patent Application Ser. No. 60/439,873, filed on Jan. 14, 2003. This Provisional Application is hereby incorporated by reference in its entirety.

BACKGROUND OF INVENTION

1. Field of the Invention

This invention relates generally to nuclear magnetic resonance (NMR) techniques for logging wells. More specifically, the invention relates to a method for analyzing NMR data utilizing a maximum entropy principle.

2. Background Art

Several inversion algorithms are available for analysing NMR well-logging data. The earliest methods provided one-dimensional T2 (transverse relaxation time) distributions from single measurement data assuming multi-exponential decays. Examples of these methods include the "Windows Processing" scheme disclosed by Freedman (U.S. Pat. No. 5,291,137) and the "Uniform Penalty" method (Borgia, G. C. Brown, R. J. S. and Fantazzini, P., *J. Magn Reson.* 132, 65–77, (1998)) Subsequently, acquisition schemes were devised comprising multiple measurements with different wait-times. Processing techniques were then introduced to analyse these measurements. One such method is disclosed by Freedman (U.S. Pat. No. 5,486,762).

Recently, complex NMR acquisition suites with multiple measurements having different wait times and inter-echo spacings have been implemented. Forward modeling inversion methods such as MACNMR (Slijkerman, W. F. J. et al. SPE 56768 presented at Annual SPE Conference Houston, 1999) and the Magnetic Resonance Fluid characterization (MRF) method (Freedman, U.S. Pat. No. 6,229,308) have been proposed to treat this type of data. The MRF technique utilizes established physical laws which are calibrated empirically to account for the downhole fluid NMR responses. By using realistic fluid models, MRF allows a reduced number of adjustable parameters to be compatible with the information content of typical NMR log data. Since the model parameters are by design related to the individual fluid volumes and properties, determination of the parameter values (i.e. data-fitting) leads to estimates for petrophysical quantities of interest.

The forward-model approach is affected by the validity of the fluid models employed. In "non-ideal" situations where fluid NMR responses deviate from the model behavior (oil-wet rocks, restricted diffusion), the accuracy of techniques may degrade. In some circumstances, "non-ideal" responses may be identified by poor fit-quality, in which case the fluid models can be adjusted by modifying the appropriate model parameter. However, it may not be obvious which element of the fluid model should be modified and this procedure can be inefficient, particularly for a non-expert.

For new measurement schemes such as "Diffusion Editing" (DE), in which the NMR data is substantially orthogonalized with regard to relaxation and diffusion attenuation, a processing technique based on a separable response kernel has been disclosed (Venkataramanan, L., Song, Y-Q., and Hurlimann, M., U.S. Pat. No. 6,462,542). This method does not involve any model for the different fluid responses. Instead, it analyses the data in terms of unbiased distributions of relaxation times and diffusion rates. It is attractive in that it requires no a priori knowledge regarding the fluid properties and in favorable cases provides simple graphical results that are easily interpreted even by non-experts. A potential drawback of the inversion is that its accuracy is in part dependent upon the separability of the response kernels. This can limit the range of its applicability to measurements in which the NMR response is substantially orthogonalized in each of the measurement dimensions, for example, application of the method to multiple CPMG sequences with different inter-echo spacings.

Existing processing techniques also impose non-negativity constraints on the individual distribution amplitudes and typically require selection of at least one regularization (smoothing) parameter. The non-negativity condition, based on obvious physical grounds, renders those processing algorithms inherently non-linear. Although not a problem in principle, this places demands on the stability of the selected optimization procedure and caution must be exercised to ensure acceptable repeatability of inversion results for noisy data. The noise issue is addressed by use of the regularization parameter, which ensures that resulting distributions are smooth. However, selecting an appropriate value for the regularization parameter is not trivial. Despite the considerable body of published work addressing the question of regularization from a theoretical point of view (e.g. see references cited in Borgia, G. C. Brown, R. J. S. and Fantazzini, P., *J. Magn Reson.* 132, 65–77, (1998) and Venkataramanan, L., Song, Y-Q., and Hurlimann, M., U.S. Pat. No. 6,462,542 ), in practice regularization remains largely subjective, sometimes based only on the aesthetic appearance of the computed distributions. Regularization is of particular importance in multi-dimensional inversions, since the distributions are generally grossly underdetermined by the data and noise artifacts can easily result. In addition, different regions of the distributions display vastly different sensitivity to the input data. Failure to account for these variations in sensitivity can lead to false or unrealistic peaks in the distributions which can easily be misinterpreted.

SUMMARY OF INVENTION

According to one aspect of the disclosed subject matter a method is described extracting information about a system of nuclear spins from data taken on a sample of an earth formation. Specifically, a set of NMR data is acquired for a fluid sample located either in a borehole or in a laboratory environment. From the set of NMR data, a multi-dimensional distribution is calculated using a mathematical inversion that is independent of prior knowledge of fluid sample properties.

According to another aspect of the disclosed subject matter, a multi-dimensional distribution is calculated using a mathematical inversion that is independent of prior knowledge of fluid sample properties and is independent of any specific acquisition sequence.

DETAILED DESCRIPTION OF THE PREFERRED EMBODIMENT

In general a processing method is disclosed for self-consistently treating multi-measurement NMR data to derive relatively unbiased multi-dimensional distributions which can be used for determining fluid NMR response parameters or as a basis for direct petrophysical interpretation.

The maximum entropy principle (MEP) method for processing multi-dimensional data overcomes the limitation of separable kernels and handles regularization in a simple systematic manner without the need for any user input, regardless of the noise levels of the data or the nature of the underlying distributions. It provides a simple graphical representation of the data that can be used to identify fluid responses in all environments. The graphical representations (i.e. multi-dimensional distributions) can themselves be used directly for interpretation or alternatively they may be used to guide the selection of parameters for model-based processing such as MRF. It is important to recognize that the MEP technique as well as the methods to interpret D-T2 maps are applicable to CPMG (Carr, Purcell, Meiboom, and Gill) and DE (diffusion editing) measurements, or any other NMR measurement scheme that responds to spin relaxation rates, molecular diffusion and combinations of these properties.

The response, A, from a three-dimensional measurement can be expressed as $$A(\tau_1, \tau_2, \tau_3) = \sum_i \sum_j \sum_k f(i, j, k) H(\tau_1, \tau_2, \tau_3; i, j, k) + \delta(\tau_1, \tau_2, \tau_3) \quad (1)$$

where $\tau_1, \tau_2, \tau_3$, are three acquisition parameters which define a particular measurement, $f(i,j,k)$ is the amplitude of the component $i, j, k$ in a 3-dimensional distribution (i.e. each dimension corresponds to a particular property), $H(\tau_1, \tau_2, \tau_3; j, k)$ is the response of that component to the measurement specified by parameters $\tau_1, \tau_2, \tau_3$, and $\delta$ is a random noise term. Note that the number of dimensions in the distribution need not be the same as the number of dimensions in the acquisition. To place Eq. (1) in context, $\tau_1$, $\tau_2$ and $\tau_3$ could, for example, be wait time (WT), inter-echo spacing (TE) and time (t) in a CPMG measurement. Similarly, index i might refer to a particular T2 value, T2(i), j may refer to a diffusion rate, D(j), and k might correspond to a particular T1 value or T1/T2 ratio, R12(k).

The solution of Eq. (1) consists of determining $f(i,j,k)$ given a series of measurements, $A(\tau_1, \tau_2, \tau_3)$, assuming that the form of $H(\tau_1, \tau_2, \tau_3; i, j, k)$ is known. At first this may appear to be straightforward since we typically acquire several thousand echoes in a multi-measurement NMR sequence, whereas the distribution might be adequately defined by, say, 20×20×10=4000 components. In other words, the number of measurements (i.e. echo amplitudes) is comparable to or more than the number distribution components. In reality, the inversion described by Eq. (1) is grossly under-determined because the response kernels $H(\tau_1, \tau_2, \tau_3; i, j, k)$ are substantially linearly dependent. In fact, even comprehensive multi-measurement data with good signal-to-noise can often be described by as few as 10 parameters, implying that the data could be compressed to just 10 independent components without any significant loss of information.

The problem of deriving extensive distributions from limited datasets arises in many areas of science. One interesting and relevant example of this is the determination of molecular distribution functions. In this case, a small number (sometimes just one) of measured moments, $\overline{M}_n$, of a distribution may be available, from which an entire, distribution is to be calculated. Information theory (E. T. Jaynes, Phys. Rev. 106, 620 (1957)) states that in such a situation, the "most probable" distribution is $$f(x_i) = Z^{-1} \exp\left(\sum_n \alpha_n M_n(x_i)\right) \quad (2)$$

where Z is a normalization function and $M_n(x_i)$ are functions whose expectation values define the moments, $$\overline{M}_n = \sum_i M_n(x_i) f(x_i) \quad (3)$$

and $\alpha_n$ are parameters which are adjusted such that the moments computed using Eqs. (2) and (3) agree with the measured values. The number of parameters, $\alpha_n$, used to fit the data should not exceed the number of measured moments. Unlike conventional inversion algorithms commonly used for deriving T2 distributions, this scheme does not require any explicit regularization. This approach provides the distribution which is simultaneously consistent with all the available data and has the maximum entropy, S, as given by $$S = -k \sum_i \ln(f(x_i)) f(x_i) \quad (4)$$

where k is a constant. A simple discussion of the "Maximum Entropy Principle" (MEP) in the context of distribution functions is given in a recent book—Dill, K. A. and Bromberg, S., "Molecular Driving Forces", Garland Science Publishing, (2003).

A more specific derivation is also reproduced in most standard texts on statistical thermodynamics (eg. McClelland, B. J., "Statistical Thermodynamics", Chapman and Hall, (1973)) as part of the discussion of Maxwell-Boltzmann statistics. In that case, the "measured" quantity is the energy, E, $$E = \sum_i E(x_i) f(x_i) \quad (5)$$

and the resulting well-known distribution is $$f(x_i) = Z^{-1} \exp(-\beta E(x_i)) \quad (6)$$

where $\beta=1/kT$ (T=temperature in Kelvin) and $E_i$ is the energy of state i.

A good example of the practical application of MEP is given by Catalano, D., Di Bari, L., Veracini, C., Shilstone, G. and Zannoni, C., *J. Chem. Phys.,* 94, 3928, (1991), who derive internal rotameric distribution functions for substituted biphenyl molecules from NMR dipolar coupling measurements.

Maximum entropy principles can also be applied to deriving relaxation time and diffusion rate distributions from NMR well-log data. At least one difference is its application to deriving multi-dimensional rather than one-dimensional distributions. As demonstrated herein, the disclosed MEP approach is capable of treating such multi-dimensional distributions, which are otherwise expected to be grossly under-determined by the available data.

The first step in applying MEP is to identify a suitable set of basis functions (i.e $M_n(x_i)$) defined in the space of the distribution (eg. in T2-D space), whose mean values can be measured. It is recommended (although not strictly required) that the basis functions be orthogonal and that they can be ranked according to the degree of "detail" they contain. In other words, we expect that simple distributions with a small number of broad peaks should be defined by the first few moments. One set of functions which satisfies these requirements can be obtained by Singular Value Decomposition (SVD) of the measurement kernel, $H(\tau_1, \tau_2, \tau_3; i, j, k)$. The SVD method decomposes the kernel matrix, H, into the product of three separate matrices $$\left( H \right) = \left( U \right) \begin{pmatrix} s_1 & & 0 \\ & \ldots & \\ 0 & & s_n \end{pmatrix} \left( V^T \right) \quad (7)$$

where S is a diagonal matrix whose elements, $s_i$ are the singular values of H. The columns of U and V are known as the left and right singular vectors respectively and are orthogonal, $$\sum_{i=1}^{M} U_{ik} U_{ij} = \delta_{jk}; \quad (8)$$

$$\sum_{i=1}^{N} V_{ik} V_{ij} = \delta_{jk};$$

In order to express H as a 2-dimensional matrix, we define a general measurement co-ordinate, $\tau$, (eg. $\tau$=WT, TE(L), n) and a distribution co-ordinate, x, (eg x=T2, D, R12). From Eq. (7), we can now write $$\sum_{\tau} U_n^T(\tau) H(\tau, x) = s_n V_n^T(x) = v_n(x) \quad (9)$$

where $v_n$ are un-normalized orthogonal vectors expressed in the space (x) of the distribution function. Combining Eqs. (1) and (9), leads to the useful expression $$\sum_{\tau} U_n^T(\tau) A(\tau) = \sum_{x} v_n(x) f(x) + \delta_n = \bar{v}_n + \delta_n \quad (10)$$

Since the $U^T_n(x)$ are available from SVD analysis of H, and the $A(\tau)$ are just the measured echo amplitudes, it is straightforward to compute the $\bar{v}_n$. Note that the second part of Eq. (10) is formally identical to Eq. (3). Thus, to within some statistical noise, $\delta_n$, we can measure a set of moments, $\bar{v}_n$, of the distribution function, f(x), which are independent of each other moment within that same set. It is known that, according to SVD analysis, these moments correspond to the expectation values of a set orthogonal functions of the distribution co-ordinate, x. From the preceding discussion of the MEP method, it follows that the distribution function can be expressed as $$f(x) = Z^{-1} \exp\left( \sum_n \alpha_n v_n(x) \right) \quad (11)$$

where the parameters, $\alpha_n$, are adjusted such that the measured moments, $\bar{v}_n$, are reproduced (see Eq. (10)). The number of components, N, included in the exponent summation on the right of Eq. (11) should not be greater than the number of valid measured moments, $\bar{v}_n$. The number of valid moments can be estimated by comparing the absolute values of the moments with their estimated standard deviations. Since the moments tend to decay with increasing rank, n, it is relatively straightforward to determine at what value of n the moments become insignificant relative to noise levels. This determination of N is in contrast to inversions requiring subjective regularization that are largely indeterminate. Alternatively, N may be fixed at some reasonable value determined empirically from previous data or from modeling.

It should be noted that $Z^{-1}$ is included to comport with accepted notation of a normalization parameter. However, according to one embodiment, the normalization parameter is omitted altogether. According to another embodiment, the normalization parameter is used by normalizing the equation to a value of one. It should further be noted that although the inversion is described in terms of a set of orthogonal functions, orthogonality is merely a result of the SVD approach and is not required. An example of a non-SVD analysis is the use of Legendre Polynomials applied to single CPMG data. This concludes the general theoretical discussion of MEP with regard to deriving relaxation/diffusion distributions from NMR data.

At this point it is useful to consider specific forms for kernel, H, and derive the corresponding SVD vectors. For a general multi-measurement NMR acquisition, performed in a magnetic field gradient, G, the elements of H might correspond to the amplitude of a particular echo, n, measured with wait time (WT), and inter-echo spacing (TE). However, for multi-measurement acquisition sequences, the total number of echoes is typically several thousand, while the distribution may be defined by several hundred components. Evidently, H can become very large and cumbersome for the purposes of evaluating SVD. It is therefore expedient in practice (this is a limitation of the available processing capabilities and not of the algorithm itself) to compress the data prior to numerical evaluation. One simple compression method is to compute "window sums". Each echo train is divided into sections in which the echo amplitudes are summed (Freedman U.S. Pat. No. 5,291,137). In order to accurately represent the multi-exponential decays, window sums in the early part of an echo train generally contain small numbers of echoes and windows for latter parts of the train contain large numbers of echoes. For standard CPMG sequences acquired on the CMR tool, which has a distribution of magnetic field gradients, F(G), the window-sum kernel can be written as $$H(WT, TE, m:T2, D, R12) = \left(\frac{1}{\sigma_E\sqrt{1+n2(m)-n1(m)}}\right)\sum_k F(G_k) \quad (12)$$

$$(1-e^{-WT/(R12 \times T2)}) \times$$

$$\left[e^{-(n1(m)-0.5)TE/T2_{D,G,TE}} - e^{-(n2(m)+0.5)TE/T2_{D,G,TE}}\right]\frac{T2_{D,G,TE}}{TE}$$

$$(T2_{D,G,TE})^{-1} = T2^{-1} + \frac{(\gamma G\, TE)^2 D}{12} \quad (13)$$

where $\sigma_E$ is the noise per echo for the particular measurement, $\gamma$ is the proton gyromagnetic ratio and n1(m) and n2(m) are the first and last echoes of the mth window sum. Note that other types of compression (eg. SVD) could also be applied to the data. The resulting kernel would need to be modified accordingly.

One focus of the model-independent analysis is to provide an unbiased representation of the data. Information contained in the multi-dimensional maps is essentially identical to that contained within the original echo amplitudes. Although the maps provide a way to understand the data from an NMR perspective, they do not give a petrophysical interpretation of the results. In some cases a petrophysical interpretation may be quite straightforward from visual inspection of the maps. However, in some situations, poor resolution along T1/T2 or diffusion axes might not be sufficient to identify separate fluids which appear with identical T2 values. In order to proceed further and derive saturations and hydrocarbon viscosities, it is necessary to apply a model to the results Present multi-dimensional models (for oil and water) states, in part, that for each value of T2, the diffusion constant can assume just two possible values, which correspond to diffusion of water and oil. The water diffusion constant is a known function of temperature, T, and is independent of T2, $$D_W(T2)=D_W(T) \quad (14)$$

whereas for oil, the diffusion constant is linearly proportional to T2, $$D_O(T2)=\lambda \times T2 \quad (15)$$

In other words, present model solutions corresponds to a horizontal (water) and diagonal (oil) lines on a D vs T2 map. In standard analysis, the raw data is fit directly using the constraints of Eqs. (14)–(15). An alternative approach is to use the maps themselves as input to derive the solution. Since the information contained in the maps is essentially identical to that of the original data, the two methods of solution should be equivalent. In practice, the data is often lacking in diffusion information (i.e. resolution) and the problem then consists of re-assigning the amplitude spread in the diffusion axis of the D-T2 map to the different formation fluids. A simple approximate way to do this is to use the geometric mean diffusion rate for each T2–$D_{LM}$(T2)—computed from the maps, and redistribute the amplitude at this T2 according to the model water and oil D values. It is convenient to define an apparent water saturation at each T2 value, SX0(T2), $$D_{LM}(T2)=D_W(T2)^{SX0(T2)}D_O(T2)^{1-SX0(T2)} \quad (16)$$

$$SX0(T2) = \frac{\ln(D_{LM}(T2)/D_O(T2))}{\ln(D_W(T2)/D_O(T2))} \quad (17)$$

Separate water and oil T2 distributions, $F_{H2O}$ and $F_{OIL}$, can now be derived, $$F_{H2O}(T2_i)=SX0(T2_i) \times F(T2_i) \quad (18)$$

$$F_{OIL}(T2_i)=(1-SX0(T2_i)) \times F(T2_i) \quad (19)$$

$$F(T2_i) = \sum_j \sum_k F(T2_i, D_j R12_k) \quad (20)$$

Note that other schemes may be implemented to derive individual fluid volumes. For example, specified areas of the map associated with a particular fluid type may be integrated to derive the corresponding volumes, from which saturations can then be computed.

Figures 1, 2:
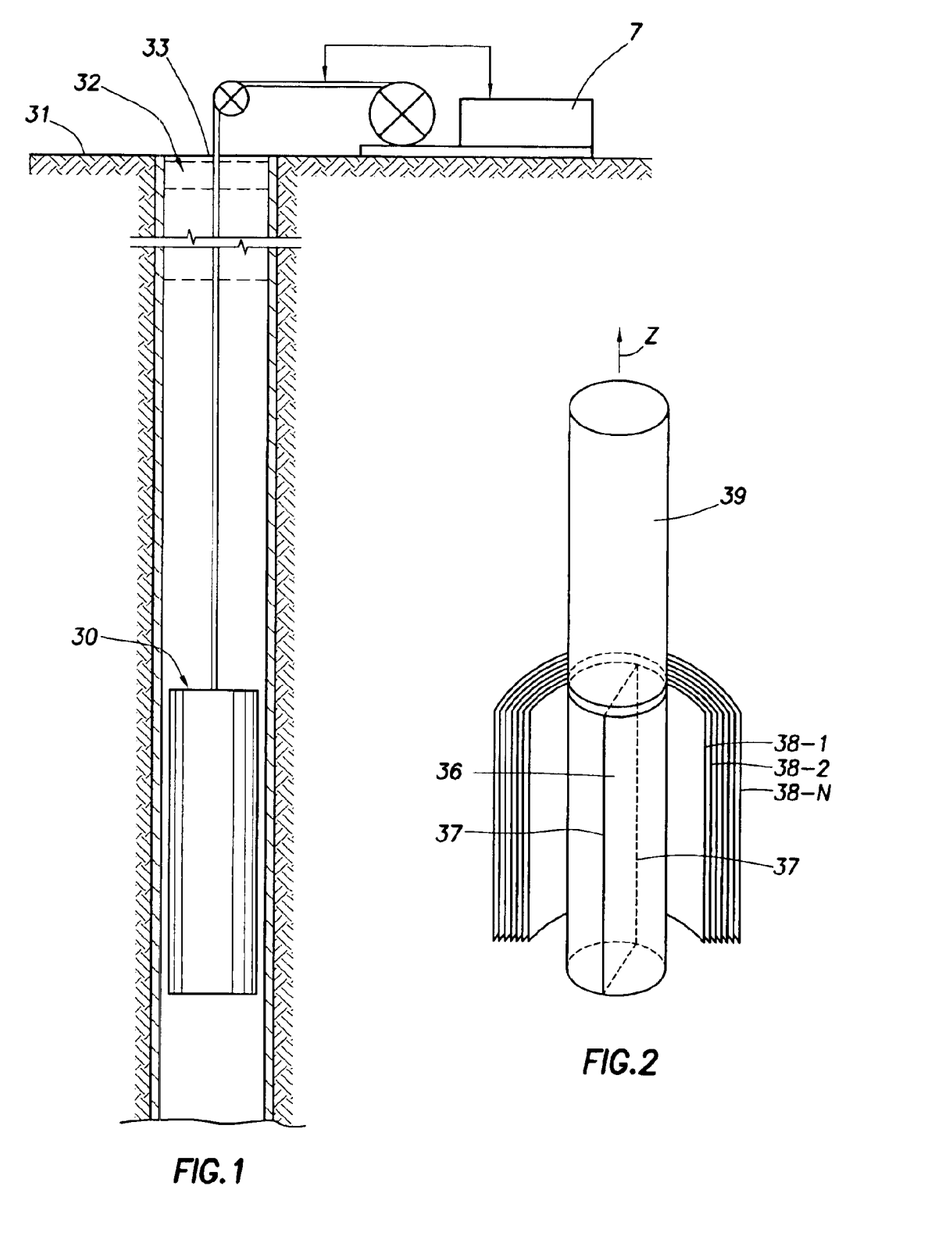
FIG. 1 is a diagram of an exemplary downhole nuclear magnetic resonance data acquisition system.
FIG. 2 is a more detailed diagram of the system of FIG. 1.

Referring to FIG. 1, there is shown an apparatus for investigating subsurface formations 31 traversed by a borehole 32, which can be used in practicing embodiments of the method of the invention. An investigating apparatus or logging device 30 is suspended in the borehole 32 on an armored cable 33, the length of which substantially determines the relative depth of the device 30. The cable length is controlled by suitable means at the surface such as a drum and winch mechanism (not shown). Surface equipment, represented at 7, can be of conventional type, and can include a processor subsystem and communicates with the downhole equipment.

The logging device which makes the measurements can be any suitable nuclear magnetic resonance logging device, for use in wireline logging applications as shown, or of a type that can be employed in measurement while drilling applications. The device 30 includes, for example, a means for producing a static magnetic field in the formations, and radio frequency (RF) antenna means for producing pulses of RF magnetic field in the formations and for receiving the spin echoes from the formations. The means for producing a static magnetic field can comprise for example a permanent magnet or magnet array, and the RF antenna means for producing pulses of RF magnetic field and receiving spin echoes from the formations can comprise for example one or more RF antennas.

An embodiment of the invention utilizes a suite of measurements from an NMR logging device of a type that can be operated to obtain separate measurements from a plurality of closely spaced thin shell regions in the surrounding formations. A simplified representation of some of the components of a suitable type of logging device 30 is illustrated in FIG. 2. The Figure shows a first centralized magnet or magnet array 36 and an RF antenna, represented at 37, which can be a suitably oriented coil or coils. FIG. 2 also illustrates a general representation of the type of closely spaced cylindrical thin shells, 38-1, 38-2 . . . 38-N, that can be frequency selected using the referenced type of multifrequency logging device. As is known in the art, for example as disclosed in U.S. Pat. No. 4,710,713, the logging device can select the shell region to be investigated by appropriately selecting the frequency of the RF energy in the transmitted pulses. In FIG. 2, a further magnet or magnet array is represented at 39, and can be utilized for applying a pre-polarizing static magnetic field to formations being approached by the investigating region of the logging device as it is raised in the borehole in the direction of arrow Z. Reference can be made, for example, to U.S. Pat. No. 5,055,788. Also see U.S. Pat. No. 3,597,681.

Figure 3:
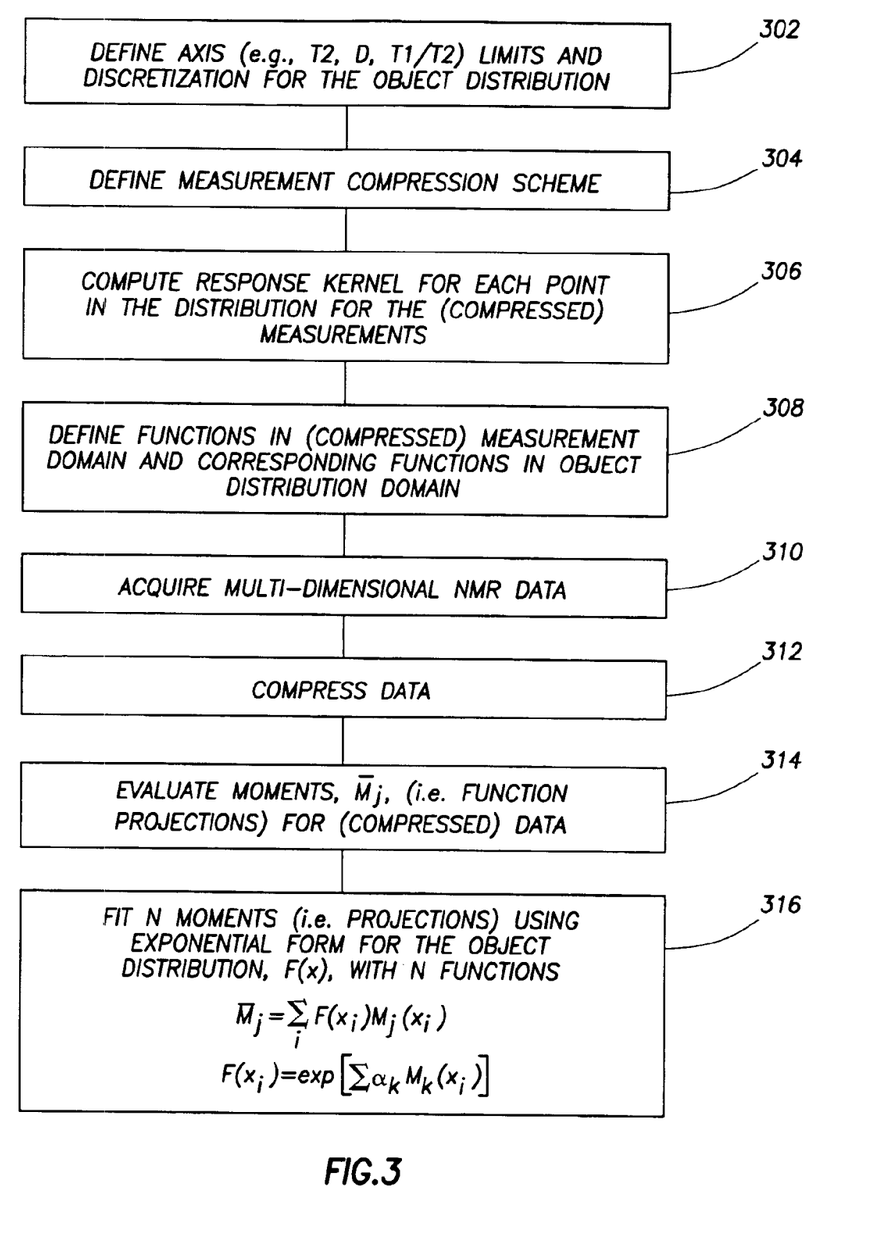
FIG. 3 is a flow diagram of the disclosed method.

Turning now to FIG. 3, shown is an exemplary flow diagram of the steps according to a disclosed embodiment. Beginning at step 302, the axis values and limits are assigned. These axes will be used to ultimately generate a multi-dimensional map of the inversion results. For example, according to one embodiment, a diffusion and an T2 relaxation axis is defined over which to display the NMR data. As mentioned, other axis values may be employed, such as replacing the T2 axis with a T1/T2, or R12, axis or T2 v. T1 or T2 v. R12 maps. Discretization is also applied to generate an object distribution. Discretization generally consists of specifying the resolution along each dimension axis. For example, in order to simplify the analysis each axis is resolved across a specified number of values along either a logarithmic or linear scale. At step 304, a compression scheme is defined. This step is primarily made necessary due to limited computing power. The MEP approach itself, however, may be applied either to compressed data or to the entire dataset. Thus, step 304 would not be necessary if sufficient computing power is available. One example of a compression scheme is the above mentioned window summing. However, many other compression schemes may be used without altering the MEP approach.

Continuing at step 306, a response kernel is computed for each data point in the object distribution. Equation 12 is one example of a response kernel equation. Specifically, H(WT, TE,m:T2,D,R12) is determined at each T2,D,R12 value for every echo (or in the case of window compression, every echo window sum). At step 308, corresponding functions are defined in both the measurement domain, (WT, TE, t) and in the object distribution domain, (T2, D, R12)of equation 1.

Acquisition of the NMR data is performed at step 310. However, the timing of the acquisition can widely vary. For example, acquisition may have occurred during some prior logging run or may be currently acquired as the MEP algorithm is applied during a logging run. Further, acquisition can be performed by any number of NMR acquisition tools, such as a wireline tool, a logging while drilling tool, a fluid sampling tool, a portable or laboratory apparatus. In addition, the MEP method is not dependent upon the acquisition sequence that is used and may be applied to, for example, data obtained in response to CPMG, CPMG modified or diffusion editing sequences.

Continuing at step 312, the dataset is compressed according the compression scheme of step 304. At step 314, the measurement domain moments (spin echo domain) $M_j$ are evaluated over the NMR data, or compressed data. This step or, alternatively, a separate step, includes a determination of the number of significant moments, N. Alternatively, a pre-defined set of N valid moments is set aside. Higher moments may be discarded at this point. At step 316, the N measurement domain moments $M_j$ are fit simultaneously using an optimization algorithm in which N parameters are adjusted independently. The N adjustable parameters are the weighting factors associated with each of the N functions in the object distribution domain which were defined in step 308. The values of these N parameters, together with their corresponding functions define a complete object distribution function, according to an exponential sum expression. The final estimate for the (multi)dimensional distribution is that for which the N computed moments most closely match the N measured moments.

According to one embodiment, a suitable optimization algorithm is shown in FIG. 3A. At step 320, an initial set of N coefficients, $\alpha_n$, is defined. At step 322, a distribution is computed for the set of $\alpha_n$ coefficients according to equation 11. A set of moments are then computed at step 324, according to Application of MEP Inversion To evaluate H, it is first necessary to specify an acquisition sequence. In this example, we consider a typical MRF acquisition comprising 6 CPMG measurements. A summary of the acquisition sequence is given in Table 1. Note that this sequence includes measurements with different inter-echo spacings and different wait times. The NMR response is modulated by T2, R12 (or T1) and D, so the appropriate inversion is 3-dimensional. The limits of the distribution axes and the number of components along each axis must now be selected. Sufficient numbers of components must be chosen to adequately describe each of the different responses given the number of measurements which discriminate these responses, whilst maintaining a small enough total number of components for acceptable numerical efficiency. Table 2 summarizes the inversion parameters used for this example. No attempt has been made to optimize the discretization scheme. However, within reasonable bounds, the details of the discretization appear to have relatively little bearing on the final inversion results.

TABLE 1

CMR acquisition sequence comprising CPMG measurements.

| Measurement | WT (s) | TE (ms) | Number of Echoes |
|---|---|---|---|
| 1 | 8 | 0.2 | 5000 |
| 2 | 3 | 2.0 | 600 |
| 3 | 3 | 0.2 | 3000 |
| 4 | 3 | 4.0 | 300 |
| 5 | 1 | 0.2 | 1800 |
| 6 | 3 | 6.0 | 100 |

TABLE 2

Parameters used for 3-dimensional inversion of multi-measurement NMR data.

| Dimension | Number of Components | Min Value | Max Value | Spacing |
|---|---|---|---|---|
| T2 | 16 | 0.5 ms | 5000 ms | logarithmic |
| D | 16 | $3 \times 10^{-11}$ m$^2$s$^{-1}$ | $3 \times 10^{-7}$ m$^2$s$^{-1}$ | logarithmic |
| R12 | 3 | 1 | 3 | linear |

1. Synthetic Data

To demonstrate the processing, four examples of synthetic data are presented. The data was generated for the acquisition sequence of Table 1 using 1 component (Tests 1 and 2) or 2 components (Tests 3 and 4) each with unique T2, D and R12 values. The total amplitude of the signal was fixed at 0.20 v/v and a random noise of 0.01 v/v was added to the echo trains. Simulation parameters are summarized in Table 3.

TABLE 3

Simulation parameters used for testing MEP inversion.

| Test No. | PHI(1) (v/v) | T2(1) (s) | D(1) (m²s⁻¹) | R12(1) | PHI(2) (v/v) | T2(2) (s) | D(2) (m²s⁻¹) | R12(2) | Noise (v/v) |
|---|---|---|---|---|---|---|---|---|---|
| 1 | 0.2 | 1.0 | 3.0e−09 | 1.0 | — | — | — | — | 0.01 |
| 2 | 0.2 | 1.0 | 3.0e−09 | 2.0 | — | — | — | — | 0.01 |
| 3 | 0.1 | 1.0 | 1.0e−08 | 1.0 | 0.1 | 0.1 | 1.0e−10 | 1.0 | 0.01 |

Figure 4:
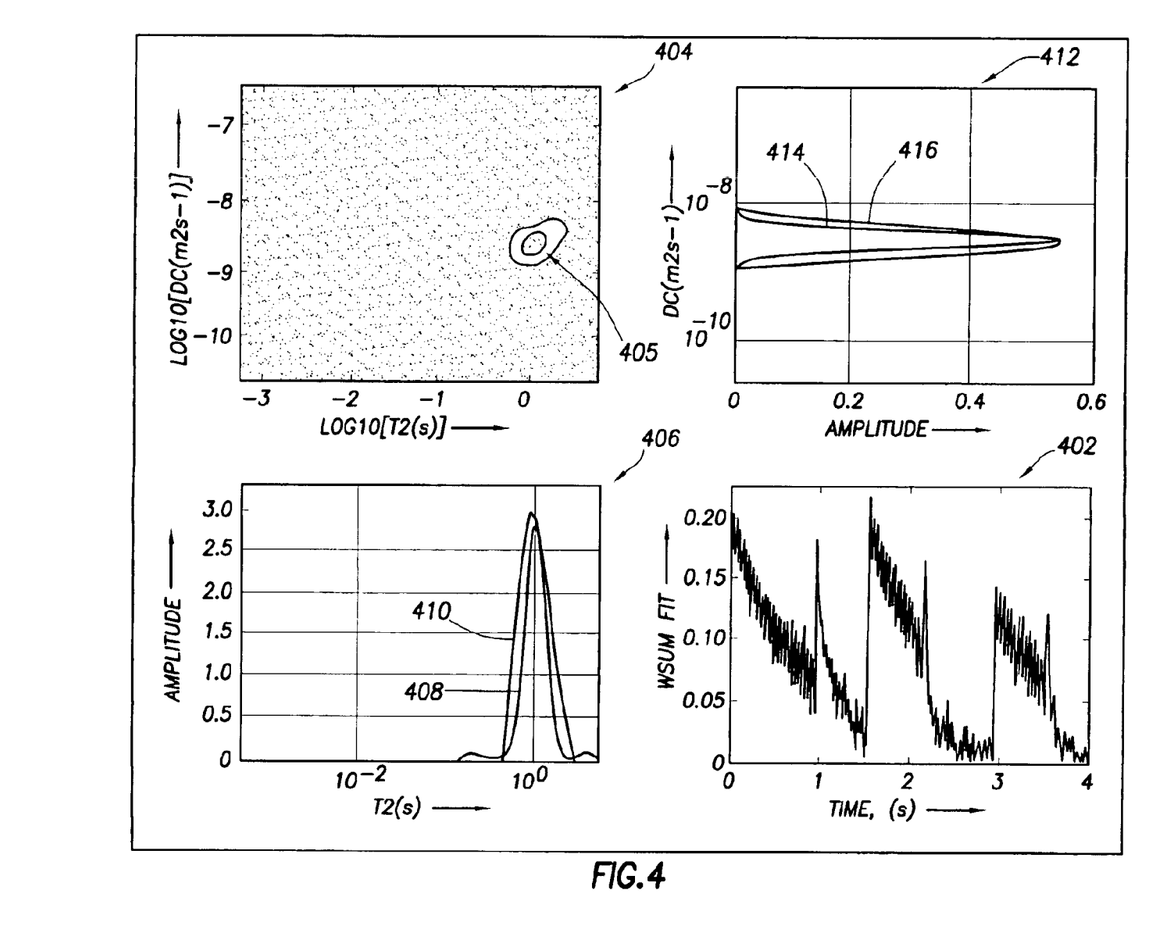
FIG. 4 illustrates a set of interpretation graphs generated based on data processed according to the disclosed method.

Results of the inversion tests are presented in FIGS. 4–7. FIG. 4 illustrates application of the MEP approach as defined in Test 1. Graph 402 shows the synthetic NMR spin echo data and the fit to the window sums derived from this data. As indicated by the y-axis, the NMR data is compressed using window summing. The graph 404 is generated based on the spin echo data of graph 402 after processing according to the MEP process. The y-axis is defined by diffusion values and the x-axis is defined by T2 values, hence a D-T2 map. The D-T2 map is derived by summing over the third dimension (R12=T1/T2). The peak 405 in graph 404 represents the probable existence of a fluid (oil, water or gas). The lower left graph 406 is the integrated T2 distribution 410 compared with the input distribution 408. The upper right graph 412 is the integrated D distribution 416 compared with the input distribution 414. The single peak 405 is represented accurately in both T2 and D axes. Just 12 SVD functions were required to achieve a good fit (to within statistical noise levels) to the data.

Figure 5:
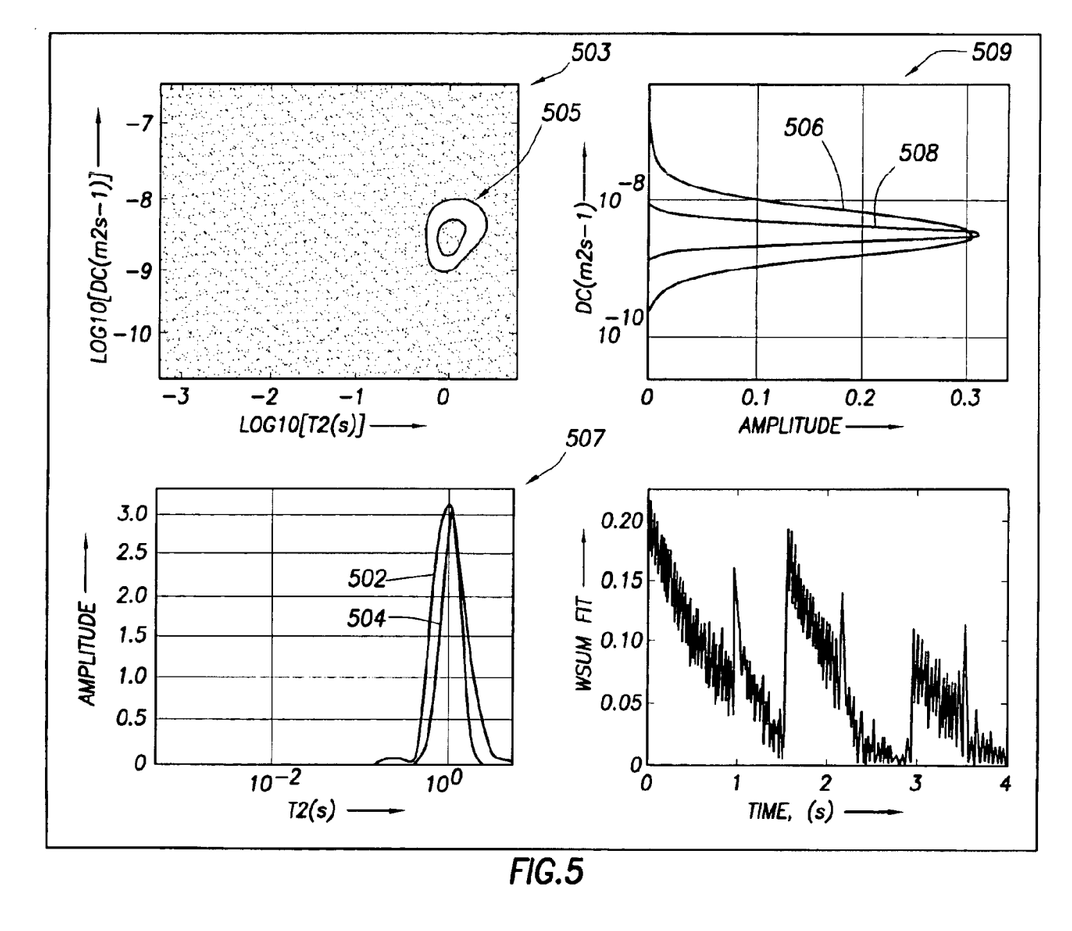
FIG. 5 illustrates a second set of interpretation graphs generated based on data processed according to the disclosed method.

FIG. 5 illustrates the results of Test 2. This simulation is identical to Test 1 except for the T1/T2 ratio, R12, which is increased to 2 in Test 2. The top left graph 503 is the T2-D map derived by summing over the third dimension (R12=T1/T2). The lower left graph 507 is the integrated T2 distribution 502 compared with the input distribution 504. The upper right graph 509 is the integrated D distribution 506 compared with the input distribution 508. Once again, the single peak 505 is represented accurately in both T2 and D axes. A slight degradation in resolution in the D axis is observed relative to Test 1 results. This may be a statistical variation due to different noise realizations in the two simulations. Again, 12 SVD functions were used to fit the data.

Figure 6:
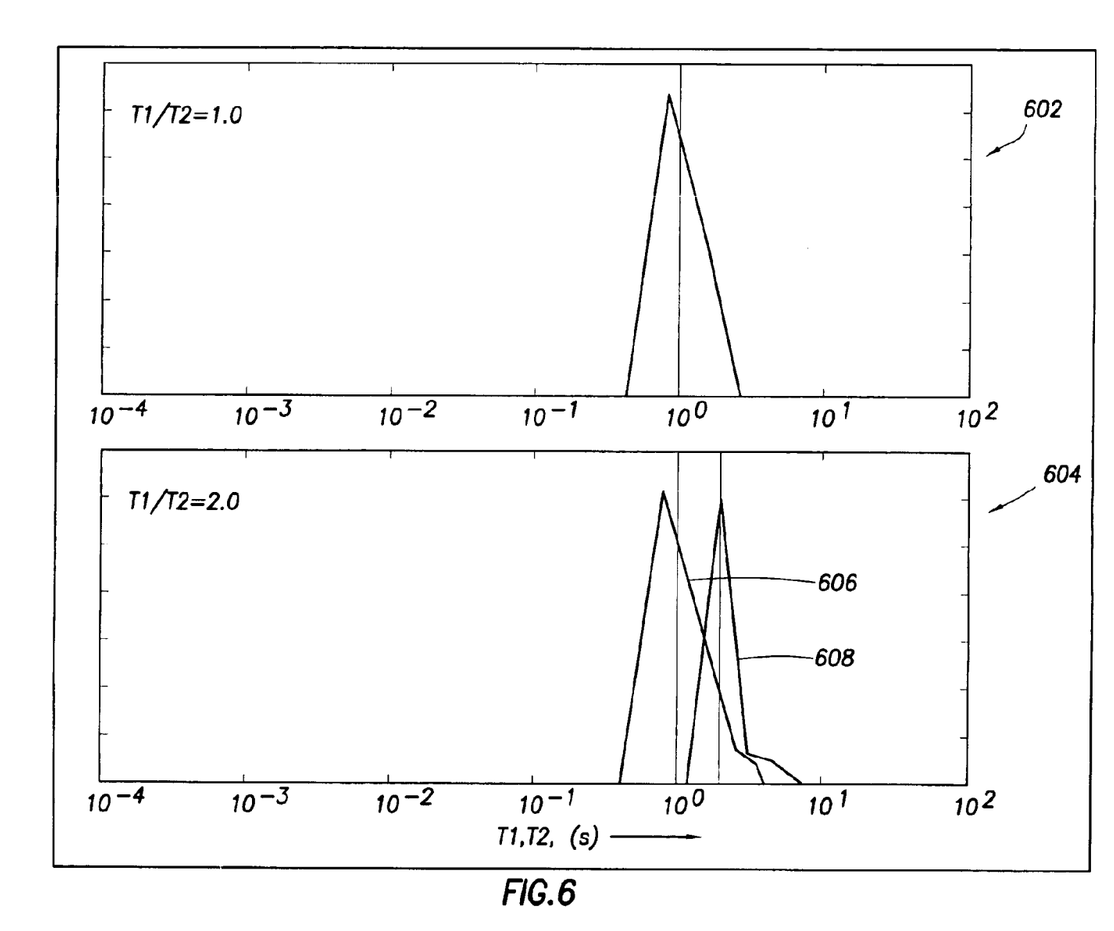
FIG. 6 is a comparison between the data of FIGS. 4 and 5.

FIG. 6 compares the T1 and T2 distributions computed for Tests 1 and 2. For Test 1, which used a put value of R12=T1/T2=1, the computed T1 and T2 distributions overlay exactly, as shown in graph 602. In contrast for Test 2, shown in graph 604, which used a value of R12=T1/T2=2, the computed T1 distribution 608 is centered at ~2 seconds, about a factor of 2 higher than the T2 distribution 606. This demonstrates that the inversion is able to accurately determine T1 values. Note that the range over which accurate T1 values may be determined is governed by the choice of wait times in the acquisition program.

Figure 7:
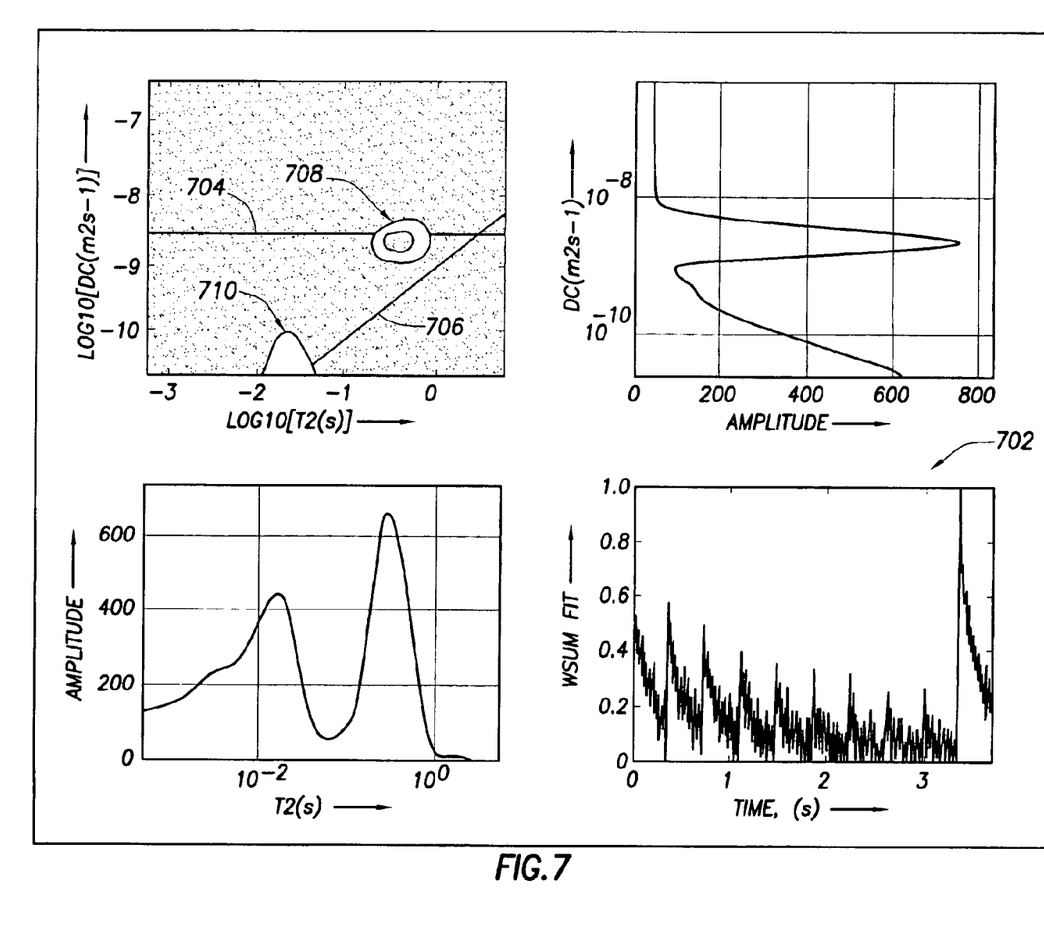
FIG. 7 illustrates another set of interpretation graphs generated based on data processed according to the disclosed method.

Results of 2-dimensional MEP inversion of diffusion editing data 702 acquired in oil-bearing sandstone formation is shown in FIG. 7. Shown at top left is the T2-D map. Overlaying are lines for water (horizontal line 704) and dead oil (faint diagonal line 706) responses. The lower left graph is the integrated T2 distribution. The upper right graph is the integrated D distribution. The diffusion editing sequence comprised 10 measurements with long echo spacings varied between 2 ms and 12 ms. A single wait time was used for all measurements, so in this case the inversion was 2-dimensional (ie. T2, D). As shown, the MEP inversion accurately resolves the two fluid instances 708 and 710 in both the T2 and D domains for this diffusion editing acquisition.

It is appropriate to again note, that according to an embodiment, the NMR processing can be performed independent of downhole operations once the data has been retrieved. For example, according to one embodiment, raw data may be processed downhole or transmitted to a surface processor concurrent with the borehole operations to obtain real time interpretation of the raw data. As is known, borehole operations may include while drilling operations as well as wireline operations occurring after the drill string has been removed from the borehole. According to another embodiment, processing may occur subsequent to obtaining the data.

A general model-independent method, based on the maximum entropy principle (MEP), has been developed that analyses multi-measurement NMR data governed by (one- or multi-dimensional) distributions of properties. The objective of the method is to present complex data in an understandable format without imposing any bias or interpretation whilst minimizing noise-related artifacts. Although the technique is quite general, it is likely to be most useful in situations where model-based analysis breaks down due to deviations of NMR properties from the "ideal" behavior assumed in the models.

The forgoing disclosure and description of the various embodiments are illustrative and explanatory thereof, and various changes to the NMR acquisition sequence, the logging process, the materials utilized in the antenna design, the inversion process and the order and timing of the steps taken, as well as in the details of the illustrated system may be made without departing from the disclosed subject matter.

What is claimed is:

1. A method of extracting information about a system of nuclear spins from a region of an earth formation comprising:

Performing a plurality of nuclear magnetic resonance measurements on the system of nuclear spins;

Acquiring nuclear magnetic resonance data from each of the plurality of nuclear magnetic resonance measurements;

Computing a multi-dimensional dataset from an inversion process performed on the nuclear magnetic resonance data that is independent of prior knowledge of the region and does not require a regularization parameter.

2. The method of claim 1, further comprising the step of:
Generating a multi-dimensional graph of the multi-dimensional dataset.

3. The method of claim 2, wherein the multi-dimensional graph is expressed along a set of axes selected from the group of diffusion, T1, T2 and a ratio of T1 and T2.

4. The method of claim 1, further comprising the step of:
Compressing the nuclear magnetic resonance data prior to computing the multi-dimensional dataset.

5. The method of claim 4, wherein compressing the nuclear magnetic data comprises transforming the data using a singular value decomposition.

6. The method of claim 1, the computing step further comprising the step of:

Evaluating a plurality of functions, $M_n(x_i)$, whose expectation values define the moments, $$\overline{M}_n = \sum_i M_n(x_i) f(x_i)$$

where $f(x_i)$ is the object distribution function, which is also expressed in terms of the same functions $$f(x_i) = Z^{-1} \exp\left(\sum_n \alpha_n M_n(x_i)\right),$$

where $\alpha_n$ are parameters which are adjusted such that the moments computed using $\overline{M}_n$ and $f(x_i)$ agree with the nuclear magnetic resonance data.

7. The method of claim 6, the evaluation step further comprising the steps of:

Comparing the computed moments $\overline{M}_n$ with a set of data moments obtained from the nuclear magnetic resonance values;

Determine a fit quality between the computed moments $\overline{M}_n$ and the set of data moments;

Determine a final distribution when the fit quality is within a tolerance limit.

8. The method of claim 7, the evaluation step further includes the step of:

Adjusting $\alpha_n$ to improve the fit quality.

9. The method of claim 6, wherein the computation step provides a distribution which is simultaneously consistent with all the available data and has the maximum entropy, S, as given by $$S = -k \sum_i \ln(f(x_i)) f(x_i),$$

where k is a constant.

10. The method of claim 6, wherein a number of N significant moments functions is determined based on the plurality of moments, $\overline{M}_n$, having a value above a noise level associated with the nuclear magnetic resonance data.

11. The method of claim 10, wherein the number of parameters, $\alpha_n$, used to fit the data should not exceed the number of the moment functions N.

12. The method of claim 6, wherein each moment within the computed moments $\overline{M}_n$ is independent of each other computed moment.

13. The method of claim 1, wherein the inversion process is independent of a regularization parameter.

14. The method of claim 1, wherein the inversion process is independent of a specific measurement sequence.

15. A logging apparatus comprising:

A logging tool that is movable through a borehole; and

A processor coupled to the logging tool, the processor being programmed with instructions which, when executed by the processor, perform the steps of:

Perform a plurality of nuclear magnetic resonance measurements on the system of nuclear spins;

Acquire nuclear magnetic resonance data from each of the plurality of nuclear magnetic resonance measurements;

Compute a multi-dimensional dataset from an inversion process performed on the nuclear magnetic resonance data that is independent of prior knowledge of the region and does not require a regularization parameter.

16. The logging apparatus of claim 15, the processor further performing the step of:

Generating a multi-dimensional graph of the multi-dimensional dataset.

17. The logging apparatus of claim 16, wherein the multi-dimensional graph is expressed along a set of axes selected from the group of diffusion, T1, T2 and a ratio of T1 and T2.

18. The logging apparatus of claim 15, the processor further performing the step of:

Compressing the nuclear magnetic resonance data prior to computing the multi-dimensional dataset.

19. The logging apparatus of claim 18, wherein compressing the nuclear magnetic data comprises transforming the data using a singular value decomposition.

20. The logging apparatus of claim 15, the computing step further comprises the step of:

Evaluating a plurality of functions, $M_n(x_i)$, whose expectation values define the moments, $$\overline{M}_n = \sum_i M_n(x_i) f(x_i)$$

where $f(x_i)$ is the object distribution function, which is also expressed in terms of the same functions $$f(x_i) = Z^{-1} \exp\left(\sum_n \alpha_n M_n(x_i)\right),$$

where $\alpha_n$ are parameters which are adjusted such that the moments computed using $\overline{M}_n$ and $f(x_i)$ agree with the nuclear magnetic resonance data.

21. The logging apparatus of claim 20, the evaluation step further comprises the steps of:

Comparing the computed moments $\overline{M}_n$ with a set of data moments obtained from the nuclear magnetic resonance values;

Determine a fit quality between the computed moments $\overline{M}_n$ and the set of data moments;

Determine a final distribution when the fit quality is within a tolerance limit.

22. The logging apparatus of claim 21, the evaluation step further includes the step of:

Adjusting $\alpha_n$ to improve the fit quality.

23. The logging apparatus of claim 20, wherein the computation step provides a distribution which is simultaneously consistent with all the available data and has the maximum entropy, S, as given by $$S = -k \sum_i \ln(f(x_i)) f(x_i),$$

where k is a constant.

24. The logging apparatus of claim 20, wherein a number of N significant moments functions is determined based on the plurality of moments, $\overline{M}_n$, having a value above a noise level associated with the nuclear magnetic resonance data.

25. The logging apparatus of claim 24, wherein the number of parameters, $\alpha_n$, used to fit the data should not exceed the number of the moment functions N.

26. The logging apparatus of claim 20, wherein each moment within the computed moments $\overline{M}_n$ is independent of each other computed moment.

27. The logging apparatus of claim 15, wherein the inversion process is independent of a regularization parameter.

28. The logging apparatus of claim 15, wherein the inversion process is independent of a specific measurement sequence.

* * * * *